(12) United States Patent
Wulf et al.

(10) Patent No.: US 7,199,377 B2
(45) Date of Patent: Apr. 3, 2007

(54) OPTICAL ANALYTIC MEASUREMENT DEVICE FOR FLUORESCENCE MEASUREMENTS IN MULTISAMPLE CARRIERS

(75) Inventors: Juergen Wulf, Ueberlingen (DE); Eberhard Dietzsch, Jena (DE); Thomas Moore, Drackendorf (DE)

(73) Assignee: CyBio AG, Jena (DE)

( * ) Notice: Subject to any disclaimer, the term of this patent is extended or adjusted under 35 U.S.C. 154(b) by 182 days.

(21) Appl. No.: 11/097,785

(22) Filed: Apr. 1, 2005

(65) Prior Publication Data

US 2005/0218338 A1 Oct. 6, 2005

(30) Foreign Application Priority Data

Apr. 1, 2004 (DE) .................. 10 2004 016 361

(51) Int. Cl.
*G01N 21/64* (2006.01)

(52) U.S. Cl. .................................... 250/458.1
(58) Field of Classification Search ............. 250/458.1
See application file for complete search history.

(56) References Cited

U.S. PATENT DOCUMENTS

| 5,221,958 | A | * | 6/1993 | Bohnenkamp ............. 356/318 |
| 5,355,215 | A | | 10/1994 | Schroeder et al. |
| 6,372,183 | B1 | | 4/2002 | Akong et al. |
| 6,420,183 | B1 | | 7/2002 | Krahn et al. |
| 2001/0028510 | A1 | | 10/2001 | Ramm et al. |
| 2004/0173760 | A1 | * | 9/2004 | Kino et al. ............. 250/458.1 |
| 2004/0174523 | A1 | * | 9/2004 | Uhl et al. .................... 356/318 |

FOREIGN PATENT DOCUMENTS

| DE | 33 18 376 | 1/1985 |
| DE | 40 05 245 | 8/1991 |
| DE | 197 55 187 | 6/1999 |
| DE | 198 10 615 | 9/1999 |
| DE | 199 03 506 | 8/2000 |
| DE | 299 01 464 | 8/2000 |
| DE | 199 16 748 | 10/2000 |
| EP | 0 987 540 | 3/2000 |
| EP | 1 122 576 | 8/2001 |

(Continued)

*Primary Examiner*—David Porta
*Assistant Examiner*—Mindy Vu
(74) *Attorney, Agent, or Firm*—Reed Smith LLP (57) ABSTRACT

The invention is directed to a device for optical analytic measurement in a multisample carrier, particularly for measuring fluorescence or bioluminescence. The object of the invention, to find a novel possibility for measuring fluorescence or luminescence in multisample carriers, wherein, during excitation of all of the wells, the secondary radiation of each well is measured simultaneously without impermissible contributions of background radiation which falsify the characteristic emission of the sample material, is met according to the invention in that the excitation light from a light source unit is directed on the multisample carrier coaxially in a ring-shaped manner around an optical axis wherein the optical axis is oriented in direction of a surface normal of the multisample carrier and coaxial to the direction of the readout beam path, and a ring mirror unit with at least one curved ring mirror, which is arranged coaxial to the optical axis in such a way that the excitation light; illuminates the multisample carrier homogeneously on all sides at an oblique incident angle, is provided for orientation of the excitation light on the multisample carrier.

39 Claims, 6 Drawing Sheets

FOREIGN PATENT DOCUMENTS

| | | |
|---|---|---|
| GB | 2 119 112 | 11/1983 |
| WO | WO 99/03008 | 1/1999 |
| WO | WO 01/01112 | 1/2001 |
| WO | WO 01/004608 | 1/2001 |
| WO | WO 02/068942 | 9/2002 |
| WO | WO 03/100398 | 12/2003 |

\* cited by examiner

OPTICAL ANALYTIC MEASUREMENT DEVICE FOR FLUORESCENCE MEASUREMENTS IN MULTISAMPLE CARRIERS

CROSS-REFERENCE TO RELATED APPLICATION

This application claims priority of German Application No. 10 2004 016 361.8, filed Apr. 1, 2004, the complete disclosure of which is hereby incorporated by reference.

BACKGROUND OF THE INVENTION a) Field of the Invention

The invention is directed to a device for optical analytic measurement in a multisample carrier, particularly for measuring fluorescence or bioluminescence, in which a plurality of samples are read out simultaneously for optical analysis in addition to the reaction process and excitation process. The invention is preferably applicable for analysis of biochemical or cell-based assays which require dispensing liquids into wells of the multisample carrier together with optical excitation and simultaneous readout of the samples.

b) Description of the Related Art

Particularly in biochemistry and pharmacology, it is necessary to test as many different substances as possible in microtitration plates (so-called multiwell plates or microplates as they will be referred to hereinafter for the sake of brevity) in combination with reagents and/or cells within a short period of time. This is usually carried out in the form of an assay in which it is precisely determined in what sequence and at what time the microplate with its samples must be at what location. Often, the reactions of living cells on substances of pharmacological interest are tested. For this purpose, the cells must be kept in a nutrient medium at a specified temperature and mixed with substances, kept in the incubator again for a defined period of time, and so forth. But the reverse is also possible; namely, substances are added to the wells of the microplate which hold reagents or cells.

In many cases, this preparatory handling concludes with the measurement of optical signals. For this purpose, one or more reagents are added to the cells before or during the measurement of light. Liquid is added to as many (or all) of the wells of the microplate as possible and, further, the light emission is measured simultaneously starting with the addition of liquid. In this connection, there are many competing demands when high microplate throughput is to be achieved with automatic HTS (High Throughput Screening) or UHTS (Ultra-High Throughput Screening). Since the generated light emission per well can often only be observed for a few seconds, a measurement of intensity per well with a time resolution in the range of seconds is required. However, the total measurement time over an entire microplate should be as short as possible.

Many different fluorescence measurement devices are known in the art, some of which are also outfitted with integrated liquid dispensers (so-called liquid handling).

For example, U.S. Pat. No. 6,372,183 describes a fluorescence measuring device in which liquid is dispensed. The liquid is dispensed in individual, preselected wells by means of an individual dispenser or by means of pipettes arranged in a row in order to dispense liquid simultaneously in a column of the microplate. The dispensing position is located before the measurement position spatially so that it is necessary to displace the microplate after adding liquid in order to measure the well in which the liquid has been dispensed; therefore, a time delay occurs. Accordingly, the microplate must be moved in order to dispense into additional wells, while the wells to which liquid has been added previously are measured simultaneously by a photon counter (PMT). For fluorescence measurement, a CCD array is described as detector; however, this may also be only a line counter, but the type and manner of optical imaging of the microplate is not mentioned in this regard. The measurement of the microplate in a plurality of wavelengths of the excitation light is carried out sequentially by adjusting a filter wheel. However, a procedure of this kind requires switching intervals of several seconds each and is not suited to HTS.

US 2001/0028510 describes a fluorescence arrangement in epi mode, as it is called, in which the excitation and emission are carried out coaxial to and perpendicular to the microplate. Also, an objective is described which is used for excitation and for recording fluorescence. Further, a ring light is focused on the object by a front lens of the objective. The disadvantage in this arrangement consists in that there is no separation of the excitation beam from the readout beam, i.e., tube brightening exists due to the shared use of the front lens and generates a considerable proportion of the background light. Also, WO 02/068942 discloses a fluorescence measuring device for time-resolved fluorescence measurements in which a beam splitter is used between the objective and the front lens and which therefore has the same disadvantage.

Similarly, WO 01/04608 describes a light detection device for different spectroscopic examinations (including fluorescence intensity, fluorescence duration and fluorescence polarization, etc.) in which the illumination and detection beam path, which is likewise unitary, is collimated and guided parallel to the microplate and a sensitive positioning of the illumination and detection on the individual wells is carried out by means of a movable focusing deflecting mirror. Troublesome tube brightening and background fluorescence from the supernatant sample are also inevitable in this case.

WO 01/01112 discloses an epi mode construction with a beam splitter (tube brightening), an array of microobjectives for individual illumination of every individual well, and a CCD camera. The disadvantage of the system is that there is a separate microobjective for each well so that when the microplate format changes (with an increased quantity of wells) the system malfunctions or special masks which disadvantageously limit the illumination efficiency would have to be used. The microlens array is again used to image the wells on the CCD camera with similar disadvantages (quantity of channels and quantity of pixels of the CCD).

U.S. Pat. No. 5,355,215 discloses an instrument that specifically reduces the unwanted background fluorescence of the well liquid and accordingly improves the wanted signal from a cell layer at the (transparent) base of the wells. The excitation light source impinges on the base of the microplate at an oblique incident angle from below and, in addition, the light bundle cross section per well is limited through a multi-pinhole diaphragm in order to observe the fluorescent radiation, as far as possible, only from a small section volume at the base of each well. As a general condition, an optical illumination axis or detection axis is directed at an angle to the normal direction of the microplate. However, due to the sharp divergence of the excitation bundle, the excited liquid volume in the wells is dependent upon position. This dependency on angle also occurs when a laser is used, as is also mentioned in this reference.

The problem of interfering background fluorescence is also addressed in U.S. Pat. No. 6,420,183, where an absorption dye is added to the supernatant solution and eliminates the exciting beam and the emitted radiation in the supernatant liquid over the cell layer to be observed. However, the use of absorbent dyes is also problematic because, on the one hand, their biochemical reaction is unclear and, on the other hand, the absorption in the centrate is incomplete and can ultimately also have an (undesirable) effect in the cell layer.

Another publication (DE 197 55 187 A1) describes a sequential method that simultaneously adds liquid to a well and excites and measures fluorescence. A lightguide and photomultiplier are used. The lightguide is arranged orthogonal to the sample carrier and the excitation and reagent injection are carried out at oblique angles. The sample carrier is likewise moved in order to assist in dispensing and measuring individually (or by column).

OBJECT AND SUMMARY OF THE INVENTION

It is the primary object of the invention to find a novel possibility for measuring fluorescence or luminescence in multisample arrays, wherein, during excitation of all of the wells, the secondary radiation of each well is measured simultaneously without impermissible contributions of background radiation (e.g., emission of the supernatant liquid columns or optical brightening caused by coupled in excitation light) which falsify the characteristic emission of the sample material. Further, another object consists in adding one or more liquids accompanied by continuous observation without appreciably lengthening the total duration for addition and measurement of liquids.

A further object consists in measuring various types of assays (biochemical assays, assays based on microspheres [beads] or cells) with the same device and/or measuring two or more dyes with different excitation and/or emission wavelengths.

In a device for optical analytic measurement for a multisample carrier, particularly for measurements of fluorescence or bioluminescence, wherein excitation light of at least one light source is directed to a plurality of wells of the multisample carrier and the secondary radiation emitted by the samples is directed on at least one high-sensitivity image recorder via a readout beam path by at least one optical imaging system, the above-stated object is met according to the invention in that the excitation light from the light source unit is directed on the multisample carrier coaxially in a ring-shaped manner around an optical axis, wherein the optical axis is oriented in direction of a surface normal of the multisample carrier and coaxial to the direction of the readout beam path, and a ring mirror unit with at least one curved ring mirror which is arranged coaxial to the optical axis in such a way that the excitation light illuminates the multisample carrier homogeneously from all sides under a defined oblique incident angle is provided for orientation of the excitation light on the multisample carrier.

The light source unit is advantageously constructed as a ring light source arranged coaxial to the optical axis.

In this connection, the light source unit can preferably be constructed as a bundle of light-conducting fibers arranged so as to be circularly coaxial to the optical axis.

In another advantageous construction, the light source unit can have means for generating a coaxially circular optical image which generate a coaxial ring light bundle that is directed to a ring mirror of the ring mirror unit. In this case, the light source unit preferably has a light source and at least one mirror unit which is arranged on the optical axis and which deflects the light of the light source approximately radially outward away from the optical axis and directs it to a coaxially arranged conical zone mirror, and, by means of the mirror unit and the conical zone mirror, light impinging from the light source forms coaxially around the optical axis in a slightly divergent ring light bundle that is uniformly distributed at least on time average.

In a first construction, the mirror unit has a rapidly rotating mirror whose axis of rotation is oriented coaxial to the optical axis and whose mean surface normal is oriented in such a way that the light of the light source is deflected approximately radially outward on the internally reflecting conical zone mirror, wherein the mirror executes an integral multiple of a complete revolution of the mirror around the optical axis during a preselected integration time of the image recorder so that a uniformly distributed ring light bundle is emitted by the light source unit coaxially around the optical axis.

In a second advantageous construction, the mirror unit is constructed as a roof prism rotating coaxial to the optical axis around the mean perpendicular of its base surface, and the prism executes an integral multiple of a half-revolution of the prism during a preselected integration time of the image recorder so that the uniformly distributed ring light bundle is emitted by the light source unit coaxially around the optical axis.

In a third advantageous variant, the mirror unit is constructed as an n-sided pyramid arranged coaxial to the optical axis and having a mirror-coated outer surface. The mirror unit can be a static pyramid with eight or more sides. In a preferred construction, the pyramid is rotatable around the optical axis and carries out an integral multiple of the nth part of a revolution (when n is the quantity of side surfaces of the pyramid) during a preselected integration time of the image recorder.

In a fourth arrangement, the mirror unit can have a coaxially arranged conical mirror with an externally mirror-coated outer surface.

In all four variants for realizing the mirror unit, its mirror-coated surfaces can be curved in a convex or concave manner. In this connection, in order to improve light distribution it can be advisable in addition that every convexly or concavely curved mirror-coated surface is formed from individual facets with different surface normals.

A ring mirror of the ring mirror unit advantageously has an internally mirror-coated outer surface of a body of revolution arising from rotation of a curve around the optical axis.

The body of revolution can be an ellipsoid, a paraboloid, a hyperboloid or can be formed by rotation of a different curve.

In another advisable construction, the ring mirror unit contains an internally mirror-coated conical zone mirror (generated by rotation of a straight line).

In this case, the ring mirror unit advantageously comprises an externally mirror-coated conical zone mirror and an internally mirror-coated conical zone mirror for further expansion of the ring light bundle.

In order to expand the ring light bundle, the ring mirror unit can also advantageously comprise an externally mirror-coated conical zone mirror and an internally mirror-coated outer surface of a body of revolution arising from rotation of a curve. For this latter realization, the ring mirror unit can contain a combination of an externally mirror-coated conical zone mirror and an internally mirror-coated ellipsoid mirror, paraboloid mirror or hyperboloid mirror. Further, it may be useful for the ring mirror unit to comprise a (possibly rotating) hollow body in the shape of a truncated pyramid with two to n externally mirror-coated side surfaces and an internally mirror-coated zone mirror with one of the rotational symmetries described above.

For illumination of the multisample carrier at different incident angles, the light source unit is advisably switchable to a different convergence of the coaxial ring light bundle, wherein a first mirror unit of the light source unit can be exchanged for a similar second mirror unit that differs from the first mirror unit in that its at least one mirror-coated surface has a different inclination, and wherein, because of different reflection angles of the first and second mirror unit, first and second internally mirror-coated conical zone mirrors of different diameters are arranged in the light source unit so as to be offset along the optical axis, and at least two ring mirrors are provided in the ring mirror unit at different positions along the optical axis in order to direct one of the ring light bundles of different convergence to the multisample carrier.

In another advantageous variant for switching the light source unit to a different convergence of the coaxial ring light bundle, the first and second externally mirror-coated mirror units of the light source unit are arranged at different positions along the optical axis and the first mirror unit close to the light source can be swiveled out so that the light bundle of the light source strikes the second mirror unit when the first mirror unit is swiveled out, wherein the internally mirror-coated second conical zone mirror associated with the second mirror unit is replaced by a ring mirror of the ring mirror unit. The conical zone mirror of the light source unit can be replaced by a conical zone mirror or an ellipsoid mirror of the ring mirror unit.

Two light sources with different spectral radiation on the optical axis are advantageously coupled into the light source unit.

For special applications it is useful that at least one light source in the light source unit and at least one image recorder in the evaluating beam path are outfitted with different filters. The filters can be exchangeable spectral bandpass filters, interference filters and/or polarization filters for selecting a defined polarization state.

The evaluation beam path preferably has at least one deflecting mirror for coupling out of the readout beam path in order to deflect the emission light from the multisample carrier past the ring mirrors of the ring mirror unit onto an image recorder. When using a plurality of image recorders, at least one deflecting mirror is advantageously a dichroic mirror or semitransparent mirror.

In an advantageous variant, the evaluating beam path has an image-generating lightguide for coupling out the emission light from the multisample carrier onto an image recorder outward past the ring mirrors of the ring mirror unit. A short focal length objective is provided for imaging the multisample carrier on the end of the lightguide fiber.

Further, it is advantageous when the excitation beam path and the evaluation beam path are directed to the transparent bottom of the multisample carrier and a dispensing device or pipetting device is provided above the multisample carrier for adding liquid at the same time that measurements of the emission of the samples of the multisample carrier are constantly being carried out. In the measuring position, test substance from a microplate, the so-called compound plate, can be transferred to the assay plate particularly by use of a simultaneous pipetter with, e.g., 96 or 384 pipetting tips.

The invention is based on the idea that for a high sample throughput with a plurality of individual samples on multisample carriers (microplates) the excitation of the individual samples and the recording of the secondary emission and, as the case may be, the addition of liquids should be carried out simultaneously and the secondary emission (fluorescence or luminescence) of all the samples of the microplate can be permanently detected over a long period of time by means of an image recorder (e.g., intensified camera) if possible. The epi mode, i.e., coaxial beam bundles of excitation and detection, while well-suited for homogeneous illumination of the microplate, is problematic for fluorescence measurements because of the general optical brightening (background noise). On the other hand, different bundle incidence directions of the excitation channel and detection channel have the disadvantage of inhomogeneous illumination or readout.

Therefore, the invention solves the problem of homogeneous illumination of the microplate in that a divergent ring light bundle is generated in a light source unit coaxial to the optical axis of the entire device, is directed to at least one ring mirror in the form of an internally mirror-coated, curved outer surface of a body of revolution, and is likewise arranged coaxial to the optical axis and deflected by the ring mirror onto the microplate in such a way that the excitation light is radiated coaxial to the readout beam path in a uniformly distributed manner on all sides.

The required ring light bundle can be generated in different ways. In this connection, it must be ensured that an intensive bundle which is symmetric with respect to rotation around the optical axis and homogeneous with respect to light distribution is generated in the form of a slightly divergent truncated cone shape impinging on the ring mirror. In all cases, the optical axes for excitation and detection are identical and correspond to the mean perpendiculars of the microplate and to the axis of symmetry of the entire optical construction. The rotationally symmetric ring mirrors used for illumination are zones of the outer surfaces of bodies of revolution and can be internally mirror-coated conical surfaces, ellipsoid surfaces, paraboloid surfaces, hyperboloid surfaces or surfaces of other rotating curves. The incident angles realized on the microplate reliably prevent reflections of the excitation light originating from the bottom surface of the microplate from reaching the camera objective in that the excitation and detection channels do not share any optical components and nevertheless have a common optical axis. When using ring mirrors as zones of rotationally symmetric outer surfaces of rotating curves, a parallel beam guidance is achieved on the microplate (object-side parallel beam path) and the incident angle is accordingly kept constant over the entire microplate.

Through the use of a plurality of ring mirrors, different incident angles of the excitation light can be realized so that it is possible for a greater volume to be illuminated in volume-based assays and for a smaller volume of every well to be illuminated, for example, in adherent cell-based assays (cell lines) or in deposited microspheres, with the same device.

With the solution according to the invention it is possible to measure fluorescence or luminescence in multisample arrays, wherein, with all of the wells being excited, a secondary radiation of each well is measured simultaneously without impermissible contributions of background radiation (e.g., emission of the supernatant liquid columns or optical brightening caused by coupled in excitation light) which falsify the characteristic emission of the sample material. In particular, the excitation light is radiated in a uniformly distributed manner so that there is no need for correcting to a scaled excitation level.

Further, the invention allows one or more liquids to be added for an assay without substantially increasing the total measuring period by liquid handling.

Further, different types of homogeneous or heterogeneous or cell-based assays can be measured by the same device according to the invention and/or two or more dyes can be analyzed with different excitation and/or emission wavelengths.

Above all in biological process in which the preparation can change even during the measuring period, these processes are taken into account equally in all wells during the analysis because the entire microplate is observed simultaneously.

For cell biology assays in which the kinetics of a fluorescent dye must often be measured after the addition of a pharmacologically active substance, the device according to the invention—by simultaneously measuring all of the wells—meets the requirement that the emission of the samples is measured before, during and after the substance is added. When excitation and readout of the microplate are to be carried out from below, substances and/or other liquids can be added from above, also in a plurality of wells simultaneously, or different substances and/or other liquids can be added in a noncontacting manner at defined times and in different amounts or concentrations and can be continuously observed.

For the HTS regime in particular, the advantage of multiplexing is also gained by means of this parallel measurement by a CCD camera and a high sample throughput is accordingly achieved in spite of an appreciably increased measuring time per well.

The invention will be explained in more detail in the following with reference to embodiment examples.

DESCRIPTION OF THE PREFERRED EMBODIMENTS

Figure 1:
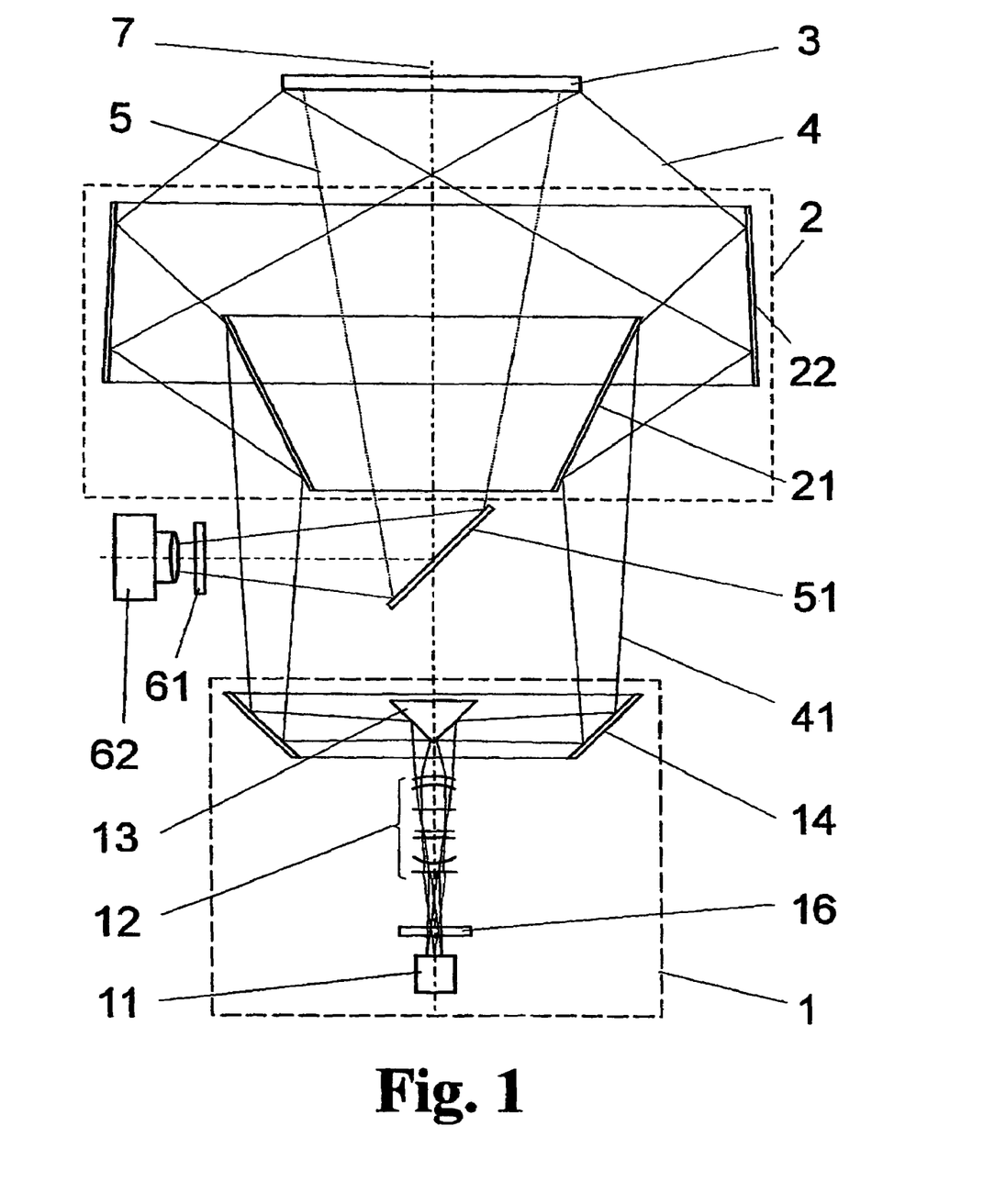
FIG. 1 shows a schematic view of the device according to the invention.

As is shown in FIG. 1, the device according to the invention basically comprises an illumination device 1 which produces a ring-shaped light bundle being enclosed between two slightly divergent cone envelopes, a ring mirror unit 2 for orientation of the excitation bundle 4 incident on the microplate 3 with at least one holder (not shown) for the microplate 3 which contains a plurality of samples to be examined, and a readout beam path 5 leading to an image recorder 6. The light source unit 1, ring mirror unit 2, microplate 3 and readout beam path 5 are arranged along a common optical axis 7 which is, at the same time, the axis of symmetry for all of the components mentioned above.

In the light source unit 1 shown in FIG. 1, the light source 11 is initially imaged into infinity by means of an achromatic objective 12. The telecentric bundle generated in this way is distributed in a rotationally symmetric manner outwardly away from the optical axis 7 on a conical zone mirror 14 so as to be dispersed on a mirror unit 13 whose axis of symmetry is coaxial to the optical axis 7, this conical zone mirror 14 likewise being arranged coaxial to the optical axis 7 as an internally reflective and truncated cone envelope. Due to the reflection at the conical zone mirror 14, a ring light is present at the output of the light source unit 1 so that a cone envelope-shaped ring light bundle 41 is formed so as to be symmetric with respect to rotation around the optical axis 7.

In order to achieve large incident angles of the excitation light on the microplate 3 and to keep the center in the surrounding area of the optical axis 7 open for large-area observation (image recording in the readout beam path 5) of the microplate 3, additional conical zone mirrors 21 and 22 are used in the ring mirror unit 2 for expanding the ring light bundle 41 on the one hand and for directing the excitation beam 4 onto the microplate 3 on the other hand. Accordingly, undesired statistical reflections at the bottom of the microplate 3 that is illuminated from below do not enter the readout beam path 5 (darkfield illumination).

Every point of the light source 11 is distributed by the mirror unit 13 in two directions away from the optical axis 7 so as to unite again at the microplate 3. Accordingly, every illuminated point of the microplate 3 receives at least two excitation beams 4 with almost opposed incident angles and the total intensity of a source point. Consequently, the light source 11 must have a beam density that is constant over the luminous area for homogeneous illumination of the microplate. Since the surface illuminated by the entire excitation beam bundle 4 is circular, its diameter must overlap the diagonal of the microplate 3 (135 mm).

The secondary emission of the samples in the wells is directed perpendicular to the microplate 3 by a deflecting mirror 51 to an image recorder 6 which can be, for example, an image intensifying camera, an intensified or cooled CCD camera or CMOS camera, or a photodiode array. The emission wavelength to be observed is selected by means of a filter 61 in front of the objective of the image recorder 6 and the excitation wavelength is adjusted by means of a spectral filter 16 following the light source 11. Both spectral filters 16 and 61 can be constructed as interference filters or as bandpass filters or can possibly be supplemented by polarization filters 63 (shown only in FIG. 6) for selecting defined polarization states and are advantageously held in filter wheels (not shown) as exchangeable filter disks.

In ray-optic calculation of optical systems, the principle of the optical axis must be taken into consideration. In centered lens optics, for example, it passes through the common axis of symmetry of all of the lenses and is, at the same time, the geometric mean of an incident centered light bundle. The optical axis 7 is then perpendicular to the individual lens surfaces and passes without interruption through the system. With respect to their coordinates and direction cosine, the individual beams of a bundle are related to the optical axis 7 as coordinate axis.

The principle of the illumination beam path will be explained with reference to FIG. 2.

Figure 2:
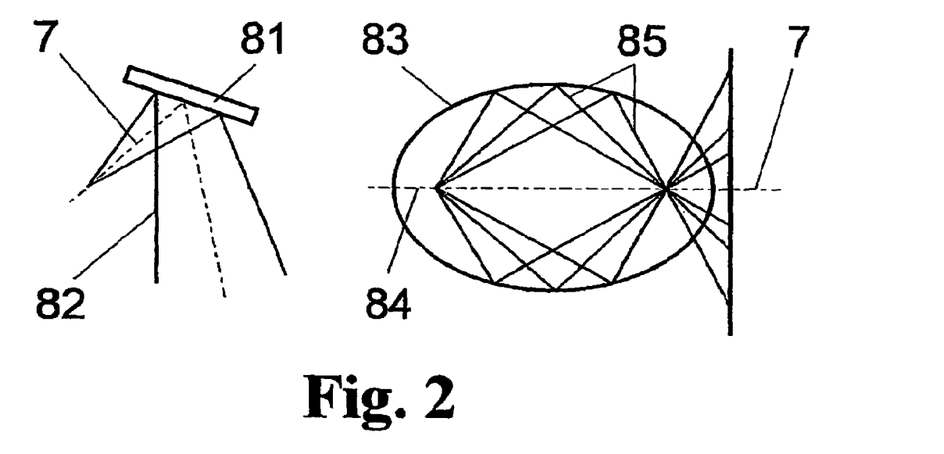
FIG. 2 shows an illustration of the principle of the optical axis according to the invention using rotationally symmetric mirror surfaces.

In mirror optics 8, according to the law of reflection, the optical axis 7 must generally be changed at each mirror 81 when the mirror 81 is not penetrated orthogonally by the optical axis 7 (see the illustration at left in FIG. 2). Due to aberrations, it does not necessarily lie in the center of a reflected light bundle 82. Moreover, the coordinate system is rotated at a mirror 81 of this kind.

An exception to this rule is provided by annular mirror bodies 83 when they are formed of outer surfaces of bodies of revolution whose axis of rotation 84 is the optical axis 7 of the entire system. When calculating differential beam bundles 85, the intersections with the mirror body 83 are calculated with reference to the optical axis 7 because the computing process proves relatively simple and efficient. In order to preserve the optical axis 7 in the center of every beam bundle 85, the mirror body 83 would have to be brought off-center and tilted in a very complicated manner and the reflection would have to be calculated and transformed back again. In addition, this off-centering and tilting depend on the respective inclination of the bundle 85, i.e., with a rotationally symmetric illumination of the entire mirror body 83, off-centering and tilting would have to be constantly recalculated. In order to avoid this, it is useful to select the optical axis 7 as axis of rotation 84 so that the mirror body 83 need not be brought out of center or tilted at all.

Figure 3:
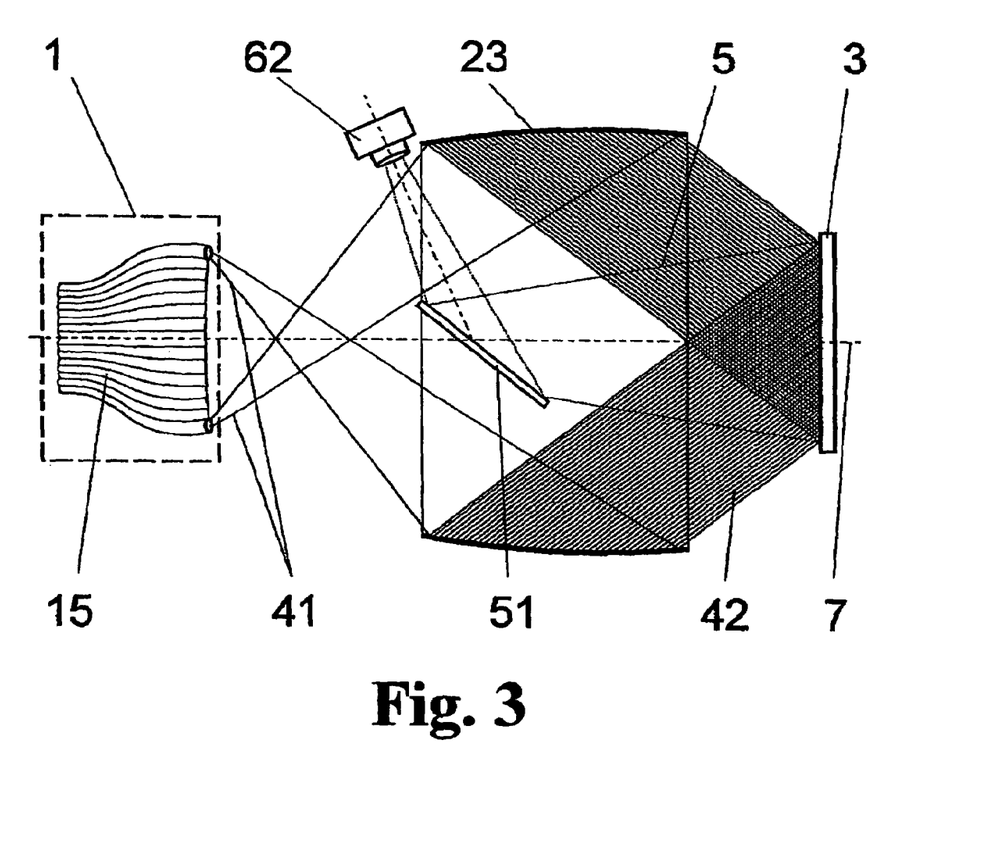
FIG. 3 shows a schematic view of the invention with telecentric beam path over a ring mirror in the form of an ellipsoid of revolution.

FIG. 3 shows another basic construction of the invention in which the light source unit 1 is simply assumed as a ring light source from which a ring light bundle 41 proceeds. The ring light bundle 41 can be generated from a lightguide ring 15 or can be imaged by suitable optics. The source location of the ring light bundle 41 is located in the left-hand focus of an ellipsoid mirror 23 of the ring mirror unit 2 which is an annular, internally mirror-coated outer surface zone of an ellipsoid of revolution.

The divergent bundle of every luminous point of the light source unit 1 is transformed into a parallel excitation bundle 42 by the ellipsoid mirror 23 in every section plane through the optical axis 7. The axis of rotation of the ellipsoid mirror 23 is again the optical axis 7 perpendicular to the microplate 3. Observation is carried out perpendicular to the microplate 3 by means of a plane deflecting mirror 51 and image recorder 6 in the form of a CCD camera 62 outfitted with a spectral filter 61.

The advantage of this construction of the device according to the invention consists in the parallel illumination of the microplate 3, i.e., the illumination conditions are identical in every well; the illumination is carried out at absolutely constant incident angles so as to be uniformly distributed about the optical axis 7. The lightguide ring 15 that is used enables a flexible setup geometry of the light source 11 (not shown in FIG. 3) and the use of small, inexpensive excitation filters (not shown).

The illumination geometry on the microplate 3 according to FIG. 3 can also be achieved in an equivalent manner when the lightguide ring 15 is exchanged for a point light source and the ellipsoid mirror 23 is exchanged for a body of revolution that is generated by a rotating elliptic arc; the elliptic arc was moved closer to the optical axis 7 so that the associated major semi-axis of the elliptic arc rotates across from it around the axis of rotation of the resultant body. Accordingly, a ring zone of a body of revolution with elliptic curvature is used which would have two points on the optical axis 7 when complete. The point light source will in turn effectively radiate only a ring light bundle 41, since the bundle must be shadowed in the center in order to generate the area without illumination for the readout beam path 5. The results of the illumination would therefore be the same as those shown in FIG. 3 as a rotationally symmetric parallel excitation bundle 42 and the illumination principle is therefore equivalent to FIG. 3.

Figure 4:
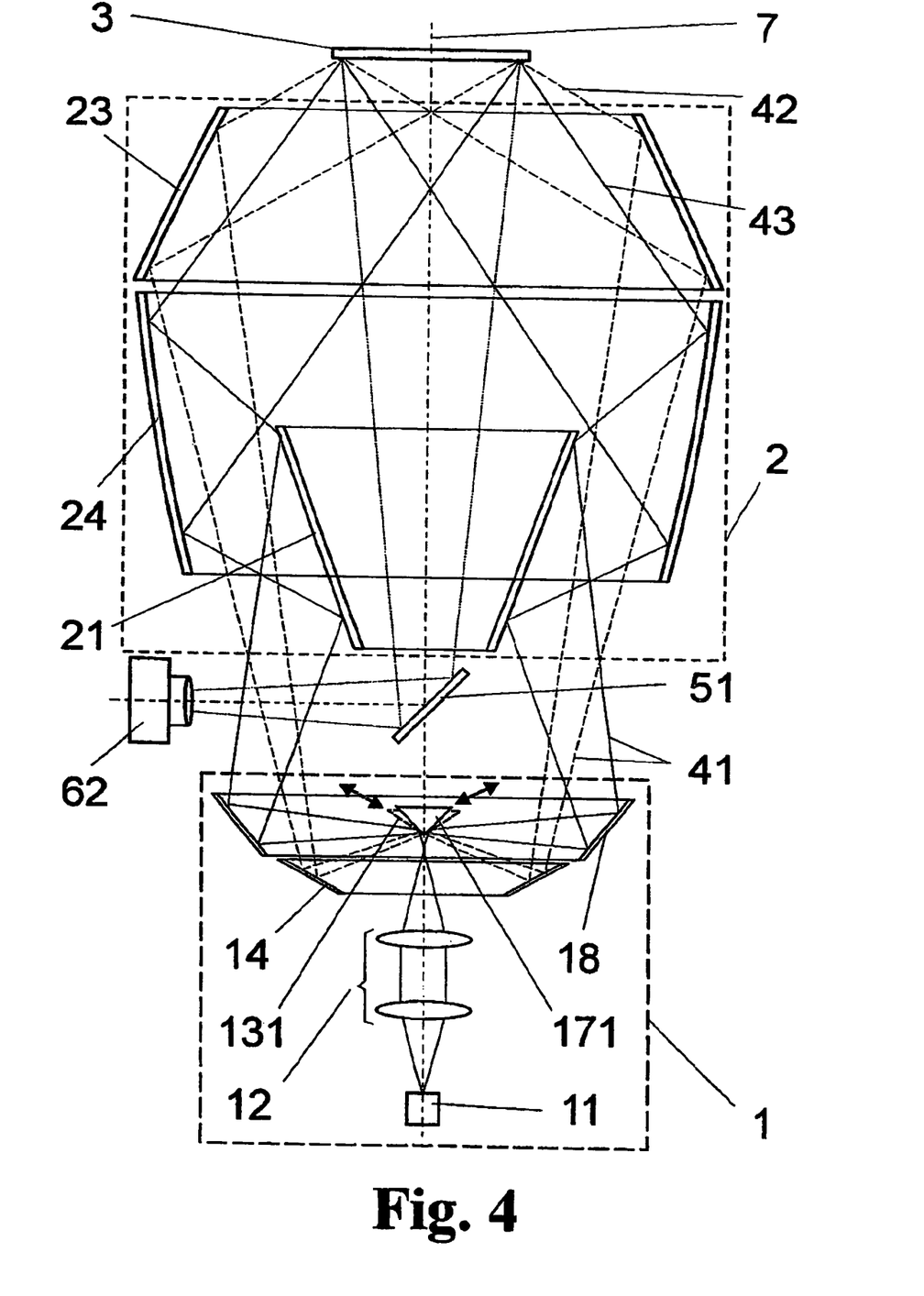
FIG. 4 shows an arrangement of the invention with telecentric illumination for generating two different incident angles of the excitation light.

The advantage of the telecentric illumination shown in FIG. 3 is expanded in the arrangement shown in FIG. 4 through the possibility of realizing two different incident angles. In this embodiment example, the light source 11 is focused in the vicinity of a first mirror unit 13, which in this case is a conical mirror 131, in order to distribute the bundle approximately radially as was described above. The divergent bundle then strikes a first conical zone mirror 14, from which it exits the light source unit 1 as a first ring light bundle 41 (shown in dashes). The first ring light bundle 41 finally reaches ellipsoid mirror 23 and is reflected on the microplate 3 as a first parallel excitation bundle 42.

By means of a switching mechanism (not shown explicitly, but represented by a dashed double arrow), the first conical mirror 131 is exchanged, as mirror unit 13, for a second mirror unit 17 in the form of a second conical mirror 171 which distributes the divergent bundle to a second conical zone mirror 18 of the light source unit 1 by means of a steeper outer surface. The second ring light bundle 41 (shown by a solid line) exiting from the light source unit 1 initially reaches an externally reflecting conical zone mirror 21 of the ring mirror unit 2 before being directed, as a second parallel excitation bundle 43, from a second ellipsoid mirror 24 of the ring mirror unit 2 to the microplate 3.

Observation (readout of the microplate emission) is again carried out in the direction of the optical axis 7 via a deflecting mirror 51 by means of a CCD camera 62.

Due to the relatively simple mechanical exchange of the two different first pyramid mirrors 131 and 171 inside the light source unit 1, switching is advantageously carried out between a first and second parallel excitation bundle 42 and 43, respectively, which have two appreciably different incident angles relative to the microplate 3 without having to move the microplate 3 to a different position or analysis device (time is saved).

Figure 5:
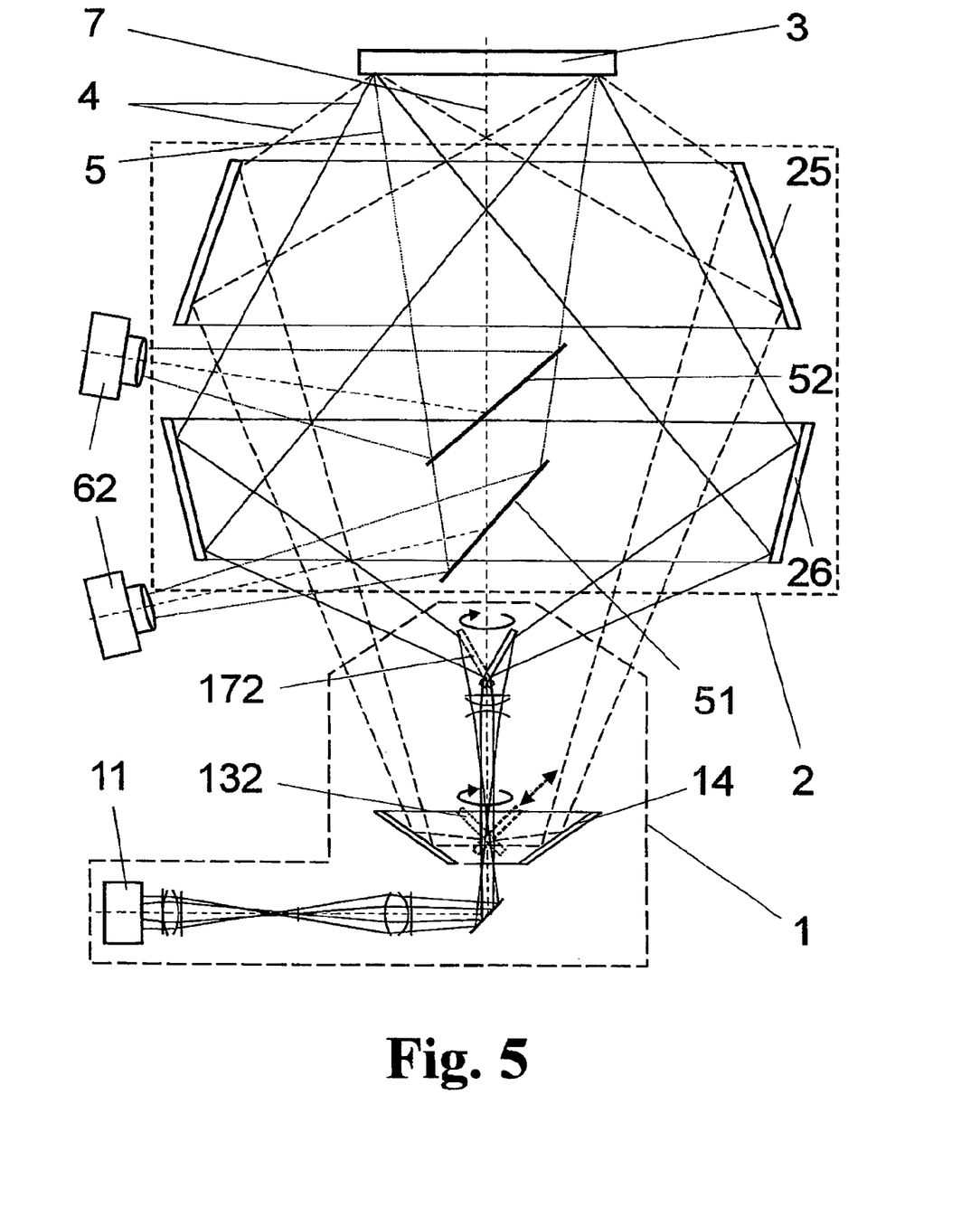
FIG. 5 shows an arrangement of the device according to the invention with conical mirrors for generating two different incident angles.

In FIG. 5, the light of the light source 11 is directed by lenses, mirrors and an exchangeable filter 16 to a first mirror unit 13 in the form of a first rapidly rotating plane mirror 132 which in turn causes a ring-shaped illumination of a first conical zone mirror 14 of the light source unit 1. The light is intentionally slightly divergent in order to limit the size of the conical zone mirror. A first conical zone mirror 25 of the ring mirror unit 2 deflects the first (shown in dashes) ring light bundle 41 from the light source unit 1 to the microplate 3 at an incident angle of about 60°.

As was already described with respect to the conical mirror 131 in FIG. 4, the first plane mirror 132 can be removed from the beam path mechanically so that the light of the light source 11 is then deflected to a second rotating plane mirror 172. From the latter, the second (shown in a solid line) divergent ring light bundle 41 can be deflected directly to a second conical zone mirror 26 arranged in the ring mirror unit 2 so that the excitation bundle 4 (solid lines) incident on the microplate 3 has an incident angle of about 33°. This beam shape enables a more economical mode of construction of the light source unit 1 because the function of the second conical zone mirror 18 (compare FIG. 4) is taken over in practice by the second conical zone mirror 26 of the ring mirror unit 2.

The intervening spaces between the conical zone mirrors 25 and 26 of the ring mirror unit 2 and between the ring mirror unit 2 and the light source unit 1 are used for reading out the emission of the samples of the microplate 3, i.e., for imaging the entire microplate 3 on the sensor chip of the CCD camera 62. The two excitation bundles 4 are optimized in such a way that reflections mirrored at the microplate 3 cannot impinge on the objective of the two CCD cameras 62. Therefore, the first observation mirror is slightly set back. In this case, the observation mirror is a dichroic mirror 52 which permits a first wavelength range to be reflected and a second wavelength range to be transmitted. Therefore, a second dye can be observed in the wells 31 (shown only in FIG. 7) of the microplate 3 by means of another CCD camera 62 on which the evaluation beam path 5 is angled by the deflecting mirror 51.

Figure 6:
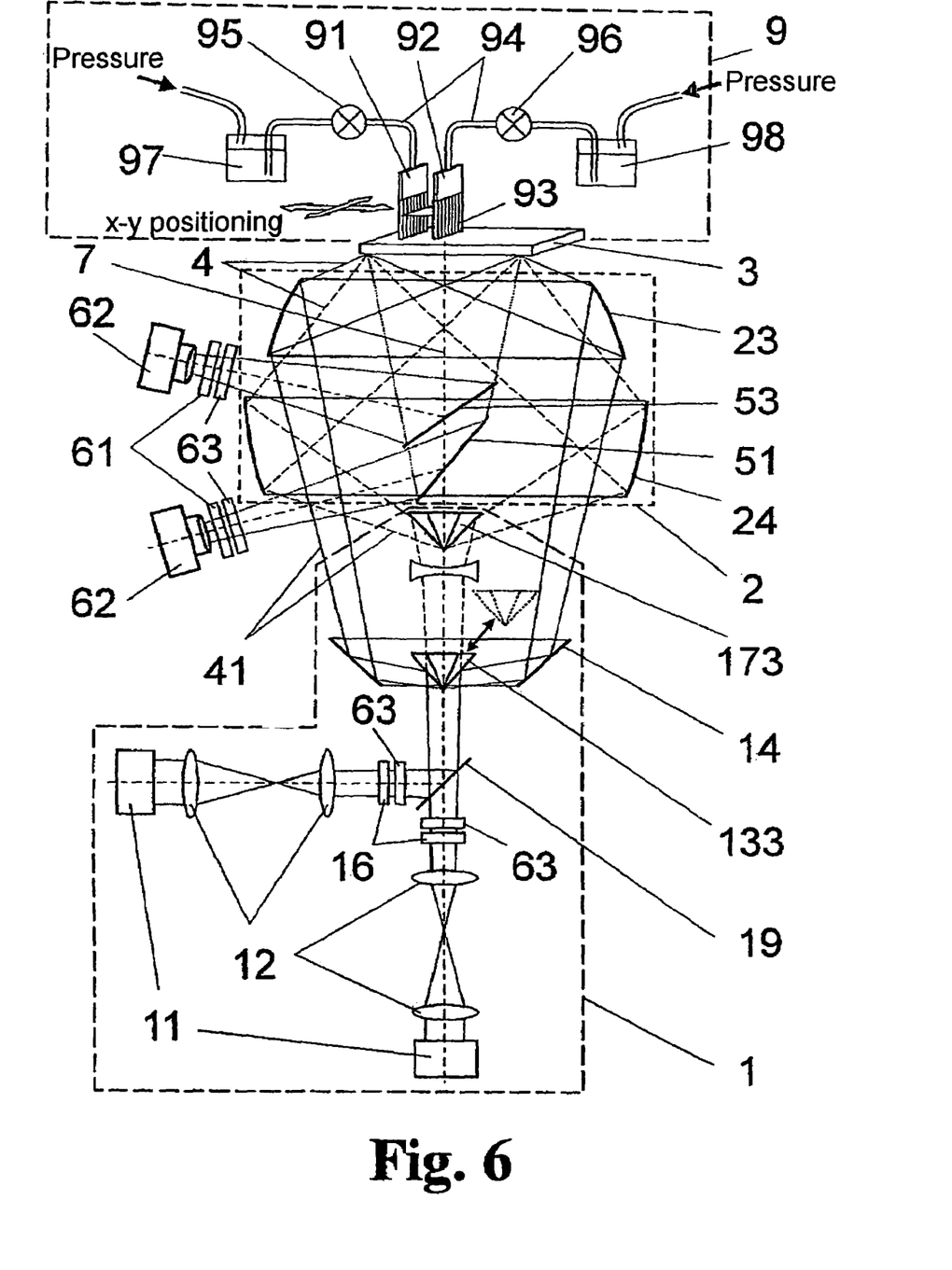
FIG. 6 shows an advantageous variant for a multipurpose use of the invention.

FIG. 6 shows the invention at a maximum level of development. A dispensing unit 9 (liquid handling) comprises two dispensing combs 91 and 92 which are coupled with one another mechanically and each of which has nozzles 93 arranged in a row, connection tubes 94 to electrically controlled valves 95 and 96, vessels 97 and 98 with the liquids to be dispensed, pressure devices (not shown) for generating a defined pressure, and an X-Y control (only symbolized by crossed double arrows) for synchronous movement of the coupled dispensing combs 91 and 92.

The dispensing combs 91 and 92 comprise individual, linearly arranged nozzles 93 which communicate, via the controllable valves (or pumps) 95 and 96, with respective vessels 97 and 98 for a determined liquid (e.g., cell cultures or reagents). A plurality of dispensing units 9 can even be used so as enable addition of different liquids. The quantity of nozzles 93 per dispensing comb 91 and 92 depends on the application and on practical aspects.

In order to be able to limit the comb movement to a direction orthogonal to the comb orientation, the dispensing combs 91 and 92 would have to have either 32 or 48 individual nozzles for a microplate 3 with 1536 wells. However, such combs are difficult and costly to produce and are more prone to malfunction at the same time, since the nozzles 93 are connected to one another by channels and, consequently, in the event of stoppage of individual nozzles 93, individual wells 31 would either not receive any liquid or incorrect volumes would be dispensed by the intact nozzles 93. Therefore, dispensing combs are limited to a maximum of sixteen, preferably only eight, nozzles 93 so that the dispensing combs 91 and 92 must be moved in both coordinate directions of the microplate 3.

The spacing of the nozzles 93 is constant and is a multiple of the smallest distance between the wells 31 of a microplate 3. There are preferably eight nozzles 93 with a spacing of 9 mm. The dispensing volume depends on the opening time of the valve 95 and 96 and can be less than 100 nl. The dispensing head comprising the two dispensing combs 91 and 92 is preferably moved back and forth over the stationary microplate 3 as is shown in FIG. 7.

Figure 7:
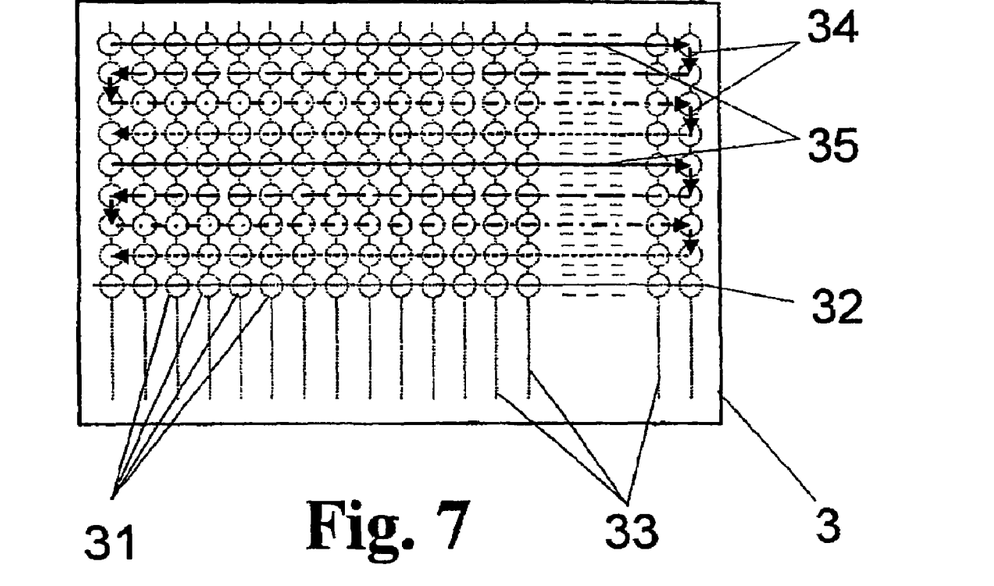
FIG. 7 shows an example for the dispensing process with a 1536-well microplate using a dispensing comb with a nozzle spacing of 9 mm.

In a schematic top view of the microplate 3, FIG. 7 shows the optimal movement path for minimizing the total dispensing time. The nozzles 93 of the dispensing combs 91 and 92 have a spacing of 9 mm so that in a 1536-well microplate 3 only the first and fifth well 31 of a column 33 are filled simultaneously. After completing a row 32 from left to right, the dispensing combs 91 and 92 move 2.25 mm in the column direction 33 so as to move back again to the left along the rows 32. This offset 34 of 2.25 mm in the column direction 33 is repeated four times until dispensing has been carried out in the entire microplate 3.

Therefore, all of the nozzles 93 of the dispensing combs 91 and 92 are guided for a very short dispensing time over the entire microplate 3 along the rows 32 in S-shaped paths 35. FIG. 7 shows the path of two nozzles 93 that are spaced apart by 9 mm and the offset 34 at the end and at the beginning of every row 32 for a 1536-well microplate 3.

The row offset 34 must be adapted to the respective microplate 3. For a 96-well microplate 3, there is no offset; the offset for a 384-well microplate 3 is 4.5 mm and is 2.25 mm for a 1536-well microplate 3. The nozzles 93 of the dispensing combs 91 and 92 can dispense very small amounts very accurately ($\approx$100 nl). This is advantageous because only small amounts of valuable materials are consumed.

According to FIG. 6, the light source unit 1 contains two light sources 11 which are coupled by a beam splitter 19 (dichroic or semitransparent). Xenon sources are preferably used because they cover the entire spectral range from UV into NIR. The light sources 11 are operated in pulsed mode as flash lights or strobe lights, but can also emit continuously. If a continuous light source 11 is used, it must be outfitted with a shutter so that the samples of the microplate 3 are irradiated only when they are to be measured. Further, both light sources 11 can be switched off by means of shutters for observing the luminescence of samples on the microplate 3.

The white light of every light source 11 is filtered monochromatically by a filter 16 in each instance. For this purpose, a plurality of interference filters are preferably arranged in a filter wheel (not shown), i.e., different excitation wavelengths can be selected so that the fluorescence of the samples of two dyes or of one dye can be observed successively in two excitation wavelengths. Further, excitation can be carried out by means of a polarization filter 63 with a defined polarization state (e.g., oriented linear polarization).

Also in FIG. 6, two different incident angles of the coaxial excitation bundle 4 can be selected on the microplate 3 in that the first mirror unit 13, which is constructed in this example as an eight-sided pyramid mirror 133, can be removed from the light bundle of the light sources 11 (symbolized by dashed double arrow) so that the light bundle of the light sources 11 impinges on a second pyramid mirror 173 and is distributed outward from the latter.

With the first pyramid mirror 133 removed, a beam path which achieves a mean incident angle of $\approx$33° on the microplate 3 relative to the optical axis 7 is used by means of the second pyramid mirror 173 and the second ellipsoid mirror 24 of the ring mirror unit 2. With the first pyramid mirror 133 slid in, the incident angle adjusted by the first ellipsoid mirror 23 is approximately 60°. The axes of symmetry of the pyramid mirrors 133 and 173, conical zone mirror 14 and ellipsoid mirrors 23 and 24 is, at the same time, the optical axis 7 of the entire optical construction, including the readout beam path 5.

In order to improve the bundle shaping and light distribution, the pyramid mirrors 133 and 173 can advantageously have "side surfaces" which are curved in a concave or convex manner and possibly segmented in addition (as facet mirrors with successive altered surface normals). The homogeneity of the light distribution can be further improved by additional rotation of the pyramid mirrors 133 and 173.

Mirroring reflections at the underside of the microplate 3 from the two excitation bundles 4 with different incident angles never reach the (plane) deflecting mirrors 51 and 53 and accordingly do not reach the CCD camera 62 for observing fluorescence (luminescence), i.e., the entire illumination optics constitute a darkfield illumination in practice.

Internally mirror-coated zones (outer surface rings) of ellipsoids of revolution, paraboloids of revolution and hyperboloids of revolution as well as bodies of other rotating curve segments, including a straight line which generates a circular cone, can be used as ring mirrors in the ring mirror unit 2. The advantage of an ellipsoid mirror is that a telecentric beam path 42 or 43 which impinges at the same angle on all sides can be directed to the microplate 3 (see FIGS. 3 and 4) and ensures a completely homogeneous illumination of the microplate 3.

As before, the emission radiation from the individual wells 31 of the microplate 3 is received perpendicular to the microplate 3 along the common optical axis 7. The gap which is visible between the two ellipsoid mirrors 23 and 24 is used for a first camera 62 that is outfitted with a spectral filter 61 and an exchangeable polarizer 63 (i.e., a polarization-optical analyzer with switching of the linear polarization state by 90°).

The first observation mirror is formed on the optical axis 7 as a semitransparent mirror 53 to enable a multipurpose use of the device according to the invention.

However, in cases where particularly weak light emission must be measured, a dichroic mirror is more advantageous because its high reflectance and transmittance for the corresponding spectral bands transmits particularly efficiently, while the semitransparent mirror 53 transmits (and reflects) only 50% and therefore considerably weakens the intensity of the emitted radiation available for evaluation.

Accordingly, a dichroic mirror 52 should be selected when the emission wavelengths to be measured lie sufficiently far apart spectrally and there are no multivalent measurement tasks to perform in which a dichroic mirror 52 whose edge wavelength cannot be altered would have to be exchanged frequently for different analyses.

A computer (not shown) which ensures the synchronization of the image recording with the excitation on the one hand and with the addition of liquid on the other hand is provided for controlling the entire device.

The problem of lost time caused by exchanging filters or the like which is known from the prior art is circumvented through the use of two strobe lights as light sources 11, each of which is adjusted to a fixed wavelength and can be switched serially very quickly (10–100 ms). Further, in addition to the two light sources 11 with different excitation wavelengths, it is possible to observe the fluorescence at a fixed emission wavelength or to use two cameras in order to measure at different emission wavelengths with differentiated sensitivity.

Further, the wavelength and/or polarization state of the excitation beam path 4 can be selected in that different spectral filters 16 and polarization filters 63 (for generating defined polarization states of the excitation light 4) are changeable by means of filter wheels in the light source unit 1. When filter changing devices of this kind are also provided in the readout beam path 5, the (fluorescent or bioluminescent) emission of samples on the microplate 3 can be examined under different excitation and detection conditions.

When the optical analytic measurement device is outfitted with a liquid station for adding liquids (dispensing unit 9), it is particularly advantageous that the emission measurement is carried out when the microplate 3 is stationary and observed in its entirety when movable dispensing combs 91 and 92 which deposit a defined amount of liquid in individual wells 31 (preferably a plurality of wells 31 simultaneously) in a noncontacting manner are moved over the microplate 3. Accordingly, there is no delay due to the displacement of the microplate 3 after individual additions of liquid because every targeted well 31 of the microplate 3 is always located above a measuring position (i.e., in the readout beam path 5) during the dispensing.

Application Example: Fura Analysis

In an embodiment form of the invention, according to FIG. 6, using two (pulsed) light sources 11 with defined excitation wavelengths, a quantitative determination of determined ions, e.g., calcium, can also be undertaken as will be explained more precisely in the following example (Fura analysis).

In cell biology, the transient intracellular calcium concentration is of interest because it supplies information about the viability of a cell. The fluorescent dye, Fura III, makes it possible to quantify the concentration of calcium when excited at 340 nm and 380 nm and the emission is observed in each instance at 520 nm. The device shown in FIG. 6 is constructed in such a way that it also permits this Ca measurement. The requirements are met by two strobe lamps—adjusted to 340 nm and 380 nm, respectively—and camera observation at 520 nm. The quotient of the two signals which are measured roughly simultaneously represents the Ca concentration (when the signal remains constant at 380 nm).

When the time resolution of the measurement is not critical, the excitation beam of a light source 11 could also be switched between two bandpass filters of 340 nm and 380 nm by means of a filter wheel.

The possibility in the design variant in FIG. 6 for dispensing two different liquids implies that two different emission wavelengths can also be observed. This is likewise provided by means of a second camera 62 in FIG. 6. In theory, the bundle that has already been divided once could even be further divided by a beam splitter 53 or dichroic mirror 52 and another camera 62 could be used.

Another advantage consists in the axial, i.e., rotationally symmetric, illumination of the microplate 3 using the principle of darkfield illumination. Accordingly, the excitation beam, which is increased by multiple powers of ten ($\approx 10^5$–$10^7$), cannot reach the emission channel (evaluation beam path 5) by mirroring reflections and the rotational symmetry of the incident excitation bundles 4 ensures a homogeneous illumination, so that a (possibly erroneous) correction to a scaled excitation level can be omitted.

The dispensing combs 91 and 92 permit the addition of very small defined volumes. This is advantageous because a) the consumption of complex pharmacological bioreagents which are often very expensive can be limited and b) a concentration series can be formed by means of programmed addition of different volumes in successive wells 31.

The possibility of realizing two incident angles of the excitation bundle 4 on the microplate 3 is particularly advantageous when the incident angle is adapted to the measurement problem. For example, when a signal from a single cell layer is to be examined, a large incident angle is selected which extensively suppresses the background signal from the volume. But if the response signal from the volume is expected, the smaller incident angle is selected. The sequential measurement of the two incident angles in a microplate 3 makes it possible to determine and subtract the influence of fluorescence from a residual volume.

Many fluorescent molecules are fixedly coupled chemically to rigid structures. In this case, the absorption depends upon the polarization of the incident excitation bundle 4 and the emission is also polarized by the retarded movement of the molecules. The construction according to FIG. 6 makes it possible in such cases to also measure a polarization of the fluorescence emission in order to gain information about the molecules (diffusion, coupling, etc.). In practice, linearly polarized light is radiated for this purpose and the emission of parallel-polarized and perpendicular-polarized light is measured. The polarization filter 63 for the emission radiation is quickly changed or rotated for this purpose.

Figure 8:
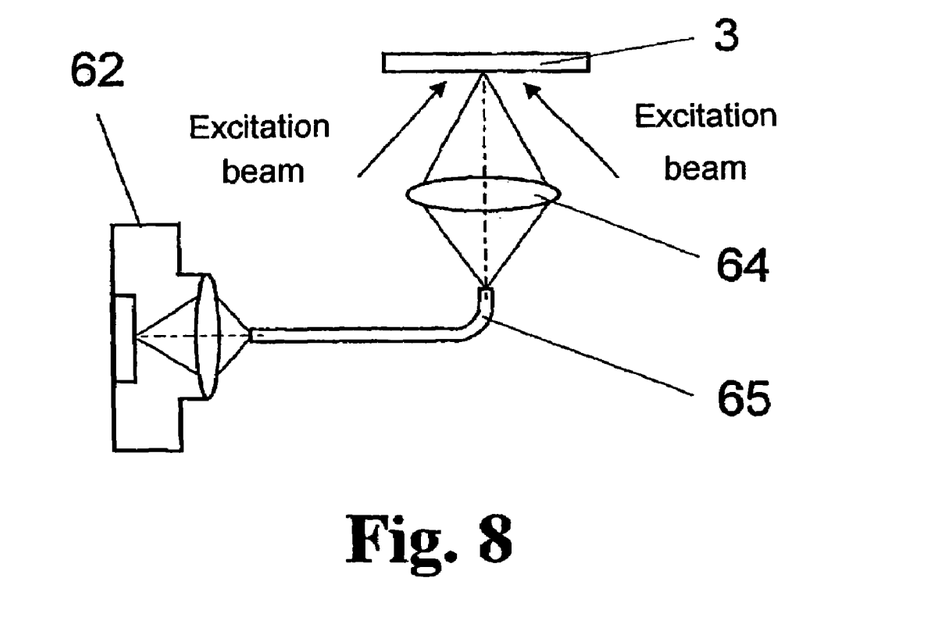
FIG. 8 shows a specially designed detection channel for image recording of the secondary emission generated by the samples in the wells of the microplate.

In order to bring the image recording closer to the microplate 3, a short focal length objective 64 which generates an image on an image-generating lightguide 65 is used according to FIG. 8. This lightguide 65 guides the emitted light out of the excitation beam path 4 in the immediate vicinity of the point of origin. The other end of the lightguide is imaged on the image converter of the camera 62. The advantage of this construction is the higher yield of emitted light compared to FIGS. 1, 3, 4, 5 and 6, and all of the previous constructions can be modified in this way.

Further, carrying out the readout beam path 5 with an image-generating lightguide 65 according to FIG. 8, which can substitute for the costly (because of its large size) mirror output-coupling, improves the signal-to-noise ratio because the emission can be measured from a short distance and with a large solid angle.

While the foregoing description and drawings represent the present invention, it will be obvious to those skilled in the art that various changes may be made therein without departing from the true spirit and scope of the present invention.

REFERENCE NUMBERS 1 light source unit
11 light source
12 objective
13 (first) mirror unit
131 (first) conical mirror
132 (first) rotating plane mirror
133 (first) pyramid mirror
14 (first) conical zone mirror
15 lightguide ring
16 filter
17 (second) mirror unit
171 (second) conical mirror
172 (second) rotating plane mirror
173 (second) pyramid mirror
18 (second) conical zone mirror
19 beam splitter
2 ring mirror unit
21 expansion conical zone mirror
22 conical zone mirror
23 first ellipsoid mirror
24 second ellipsoid mirror
25 first conical zone mirror
26 second conical zone mirror
3 microplate
31 well
32 row
33 column
34 offset
35 S-shaped path
4 excitation bundle
41 ring-shaped light bundle
42 first parallel excitation bundle
43 second parallel excitation bundle
5 readout beam path
51 deflecting mirror
52 dichroic mirror
53 semitransparent mirror
6 image recorder
61 spectral filter
62 CCD camera
63 polarizer
64 objective
65 lightguide
7 optical axis
8 mirror optics
81 plane mirror surface
82 reflected bundle
83 (rotationally symmetric) mirror body
84 axis of rotation
85 beam bundle
9 dispensing unit
91, 92 dispensing comb
93 nozzles
94 connection tubes
95, 96 valves pumps
97, 98 vessels

What is claimed is:

1. A device for optical analytic measurement for a multisample carrier, particularly for measurements of fluorescence or bioluminescence, comprising:

at least one light source for providing excitation light, said excitation light being directed to a plurality of wells of a multisample carrier and secondary radiation emitted by samples in which said plurality of wells being directed on at least one high-sensitivity image recorder via a readout beam path by at least one optical imaging system;

said excitation light from the light source unit being directed on the multisample carrier coaxially in a ring-shaped manner around an optical axis, wherein the optical axis is oriented in the direction of the readout beam path; and a ring mirror unit with at least one curved ring mirror being arranged coaxial to the optical axis in such a way that the excitation light illuminates the multisample carrier homogeneously from all sides at an oblique incident angle, being provided for orientation of the excitation light on the multisample carrier.

2. The device according to claim 1, wherein the light source unit is constructed as a ring light source which is arranged coaxial to the optical axis with coaxially radiated ring light bundle.

3. The device according to claim 2, wherein the light source unit is constructed as a ring of light-conducting fibers arranged circularly coaxial to the optical axis.

4. The device according to claim 2, wherein the light source unit has means for generating a coaxially circular optical image which generate a coaxial ring light bundle.

5. The device according to claim 4, wherein the light source unit has a light source and at least one mirror unit which is arranged on the optical axis and which deflects the light of the light source approximately radially outward away from the optical axis and directs it to a coaxially arranged conical zone mirror, by the mirror unit and the conical zone mirror, light impinging from the light source forms coaxially around the optical axis in a slightly divergent ring light bundle that is uniformly distributed at least on time average.

6. The device according to claim 5, wherein the mirror unit has a rapidly rotating mirror whose axis of rotation is oriented coaxial to the optical axis and whose mean surface normal is oriented in such a way that the light of the light source is deflected approximately radially outward on the internally mirror-coated conical zone mirror, wherein the rotating mirror executes an integral multiple of a complete revolution around the optical axis during a preselected integration time of the image recorder so that a uniformly distributed ring light bundle is emitted by the light source unit coaxially around the optical axis.

7. The device according to claim 6, wherein the mirror unit is constructed as a roof prism rotating coaxial to the optical axis around the mean perpendicular of its base surface, and the prism executes an integral multiple of a half-revolution during a preselected integration time of the image recorder so that a uniformly distributed ring light bundle is emitted by the light source unit coaxially around the optical axis.

8. The device according to claim 6, wherein every mirror-coated surface of the mirror unit is curved in a concave or convex manner.

9. The device according to claim 6, wherein every mirror-coated surface of the mirror unit is curved in a concave or convex manner and is formed from individual facets with different surface normals.

10. The device according to claim 5, wherein the mirror unit is constructed as an n-sided pyramid mirror arranged coaxial to the optical axis and having an externally mirror-coated outer surface.

11. The device according to claim 10, wherein the mirror unit is constructed as an eight-sided pyramid mirror.

12. The device according to claim 10, wherein the pyramid mirror is rotatable around the optical axis and carries out an integral multiple of the nth part of a revolution during a preselected integration time of the image recorder.

13. The device according to claim 5, wherein the mirror unit is a coaxially arranged conical mirror with an externally mirror-coated outer surface.

14. The device according to claim 5, wherein the light source unit can be switched to a different convergence of the coaxial ring light bundle for illuminating the multisample carrier at different incident angles, wherein a first mirror unit of the light source unit can be exchanged for a similar second mirror unit that differs from the first mirror unit in that its at least one mirror-coated surface has a different inclination, and wherein, because of different reflection angles of the first and second mirror unit, first and second internally mirror-coated conical zone mirrors of different diameters are arranged in the light source unit so as to be offset along the optical axis, and at least two ring mirrors are provided in the ring mirror unit at different positions along the optical axis in order to direct one of the ring light bundles of different convergence to the multisample carrier.

15. The device according to claim 14, wherein, in order to switch the light source unit to a different convergence of the coaxial ring light bundle, the first and second externally mirror-coated mirror units of the light source unit are arranged at different positions along the optical axis and the first mirror unit close to the light source can be swiveled out so that the light bundle of the light source strikes the second mirror unit when the first mirror unit is swiveled out, wherein the internally mirror-coated second conical zone mirror associated with the second mirror unit is replaced by a ring mirror of the ring mirror unit.

16. The device according to claim 15, wherein the internally mirror-coated conical zone mirror of the light source unit is replaced by a conical zone mirror of the ring mirror unit.

17. The device according to claim 15, wherein the internally mirror-coated conical zone mirror of the light source unit is replaced by an ellipsoid mirror of the ring mirror unit.

18. The device according to claim 1, wherein the ring mirror is an internally mirror-coated outer surface of a body of revolution arising from rotation of a curve around an axis.

19. The device according to claim 18, wherein the ring mirror is an internally mirror-coated outer surface of an ellipsoid of revolution.

20. The device according to claim 18, wherein the ring mirror is an internally mirror-coated outer surface of a paraboloid of revolution.

21. The device according to claim 18, wherein the ring mirror is an internally mirror-coated outer surface of a hyperboloid of revolution.

22. The device according to claim 18, wherein the ring mirror unit contains an internally mirror-coated conical zone mirror.

23. The device according to claim 22, wherein the ring mirror unit comprises an externally mirror-coated conical zone mirror and an internally mirror-coated conical zone mirror for further expansion of the ring light bundle.

24. The device according to claim 22, wherein, in order to further expand the ring light bundle, the ring mirror unit comprises an externally mirror-coated conical zone mirror and an internally mirror-coated outer surface of a body of revolution arising from rotation of a curve.

25. The device according to claim 24, wherein the ring mirror unit comprises an externally mirror-coated conical zone mirror and an internally mirror-coated ellipsoid mirror.

26. The device according to claim 24, wherein the ring mirror unit comprises an externally mirror-coated conical zone mirror and an internally mirror-coated paraboloid mirror.

27. The device according to claim 24, wherein the ring mirror unit comprises an externally mirror-coated conical zone mirror and an internally mirror-coated hyperboloid mirror.

28. The device according to claim 1, wherein two light sources with different spectral radiation on the optical axis are coupled into the light source unit.

29. The device according to claim 1, wherein at least one light source in the light source unit and at least one image recorder in the evaluating beam path are outfitted with different filters.

30. The device according to claim 29, wherein the filters are exchangeable spectral bandpass filters.

31. The device according to claim 29, wherein the filters are exchangeable interference filters.

32. The device according to claim 29, wherein the filters are polarization filters for selecting a defined polarization state.

33. The device according to claim 1, wherein the readout beam path has at least one deflecting mirror for coupling out the readout beam path in order to deflect the emission light from the multisample carrier past the ring mirrors of the ring mirror unit onto an image recorder.

34. The device according to claim 33, wherein at least one deflecting mirror is a dichroic mirror when a plurality of image recorders are used.

35. The device according to claim 33, wherein at least one deflecting mirror is a semitransparent mirror when a plurality of image recorders are used.

36. The device according to claim 1, wherein the readout beam path has an image-generating lightguide for coupling out the emission light from the multisample carrier onto an image recorder outward past the ring mirrors of the ring mirror unit, wherein a short focal length objective is provided for imaging the multisample carrier on the end of the lightguide fiber.

37. The device according to claim 1, wherein the excitation beam path and the evaluation beam path are directed to the transparent bottom of the multisample carrier and a liquid adding device is provided above the multisample carrier for adding liquid at the same time that measurements of the emission of the samples of the multisample carrier are constantly being carried out.

38. The device according to claim 37, wherein the liquid adding device is a pipetting unit.

39. The device according to claim 37, wherein the liquid adding device is a dispensing unit.

* * * * *